(12) United States Patent
Hyun et al.

(10) Patent No.: US 9,227,022 B2
(45) Date of Patent: Jan. 5, 2016

(54) NEONATAL FLUID TUBING HEATER

(71) Applicant: ACACIA, INC., Brea, CA (US)

(72) Inventors: Dongchul D. Hyun, Brea, CA (US); Michael Fleury, Brea, CA (US)

(73) Assignee: Medela Holding AG, Baar (CH)

( * ) Notice: Subject to any disclaimer, the term of this patent is extended or adjusted under 35 U.S.C. 154(b) by 180 days.

(21) Appl. No.: 13/875,852

(22) Filed: May 2, 2013

(65) Prior Publication Data

US 2013/0237957 A1 Sep. 12, 2013

Related U.S. Application Data

(62) Division of application No. 13/092,582, filed on Apr. 22, 2011, now Pat. No. 8,663,161.

(51) Int. Cl.
| | | |
|---|---|---|
| *A61M 31/00* | (2006.01) | |
| *A61M 5/44* | (2006.01) | |
| *A61J 15/00* | (2006.01) | |
| *A61M 5/145* | (2006.01) | |

(52) U.S. Cl.
CPC ............ *A61M 5/445* (2013.01); *A61J 15/0026* (2013.01); *A61M 5/44* (2013.01); *A61M 5/1456* (2013.01); *A61M 2205/36* (2013.01); *A61M 2205/8206* (2013.01); *A61M 2210/1042* (2013.01); *A61M 2240/00* (2013.01)

(58) Field of Classification Search
CPC ................. A61M 2205/36; A61M 2205/8206; A61M 2210/1042
USPC ............................................ 604/516, 28, 151
See application file for complete search history.

(56) References Cited

U.S. PATENT DOCUMENTS

| 4,532,414 A | 7/1985 | Shah et al. |
|---|---|---|
| 5,250,032 A | 10/1993 | Carter, Jr. et al. |
| 7,158,719 B2 | 1/2007 | Cassidy |

(Continued)

FOREIGN PATENT DOCUMENTS

| CN | 201139844 | 10/2008 |
|---|---|---|
| CN | 201814947 | 5/2011 |

OTHER PUBLICATIONS

Paragon Medical; "Fluid Warmers", Feb. 10, 2011; 3 pages.
www.ncbi.nlm.nih.gov; "Effect of Enteral Feeding Temperature on Feeding Tolerance in Preterm Infants"; Dec. 31, 2010; 1 page.
www.zawya.com; "GE Healthcare's New Transportable Power Source Showcased at Arab Health Strengthens Neonatal Care"; Jan. 28, 2011; 4 pages.

*Primary Examiner* — Phillip Gray
(74) *Attorney, Agent, or Firm* — Stetina Brunda Garred & Brucker

(57) ABSTRACT

A heating system for warming nutritional liquid fed to a neonate or preterm infant may comprise a control module and a heater. The heating system is portable so that the heating system is not connected to a syringe pump or other device used to feed the neonate. The heater of the heating system is mounted to the tube that is used to feed the neonate. The heater is positioned along the tube in close proximity to the neonate so that a temperature drop of the nutritional liquid after the nutritional liquid exits the heater and reaches the neonate is negligible. The heater raises the temperature of the nutritional liquid to a target desired temperature (e.g., body temperature of the mother and neonate or to a temperature above the temperature of the mother and neonate) so that the neonate may consume warm nutritional fluid. Once the nutritional liquid reaches the neonate, the nutritional liquid is at about the body temperature of the mother or neonate or at least above room temperature.

4 Claims, 5 Drawing Sheets

(56) References Cited

U.S. PATENT DOCUMENTS

| | | |
|---|---|---|
| 8,663,161 B2 | 3/2014 | Hyun et al. |
| 2004/0073161 A1 | 4/2004 | Tachibana |
| 2005/0008354 A1 | 1/2005 | Cassidy |
| 2005/0209563 A1* | 9/2005 | Hopping .................. A61M 1/28 604/151 |
| 2008/0119782 A1* | 5/2008 | Steinman .......... A61M 5/14526 604/28 |
| 2008/0262409 A1 | 10/2008 | Derrico et al. |

* cited by examiner

NEONATAL FLUID TUBING HEATER

CROSS-REFERENCE TO RELATED APPLICATIONS

The present application is a divisional of U.S. patent application Ser. No. 13/092,582 entitled NEONATAL FLUID TUBING HEATER filed Apr. 22, 2011, the entirety of the disclosures of which are expressly incorporated herein by reference.

STATEMENT RE: FEDERALLY SPONSORED RESEARCH/DEVELOPMENT

Not Applicable

BACKGROUND

The embodiments disclosed herein relate to a heater for warming nutritional liquid fed to a pre-term infant.

Nutritional delivery to a preterm infant or enteral feeding is an important part of caring for the preterm infant in neonatenatal intensive care units. Typically, the preterm infant is fed with a feeding tube that delivers breast milk or neonatal formula directly into the stomach of the preterm infant. The feeding tube is generally introduced either through the nose (i.e., nasally) or through the mouth (i.e., gastrically). Previously, the breast milk or neonatal formula was fed to the neonate while the breast milk or neonate formula was at room temperature (i.e., below body temperature). However, studies have shown that preterm infants respond favorably when the nutritional liquid (e.g., breast milk or neonatal formula) coincides with the body temperature of a person (i.e., 98.6° F.). When the nutritional liquid is provided to the preterm infant at a temperature closer to the body temperature of a person, the preterm infant was found to digest more of the nutritional liquid. Moreover, other studies have found that the lower the body temperature of the preterm infant, the higher the likelihood of mortality of the preterm infant. As such, it is important to preserve the preterm infant's energy so that the preterm infant does not need to divert energy away from heating and growth to generate heat. If the nutritional liquid is fed to the preterm infant at room temperature, the preterm infant must divert energy that could be used for healing and growth to heat him or herself due to digestion of the cold nutritional liquid. Accordingly, it would be beneficial to feed preterm infants with nutritional liquid raised to the body temperature of a person to reduce the amount of energy diverted away from healing and growth to digestion and heat generation.

In response, prior art devices have been introduced for warming nutritional liquid (e.g., breast milk or neonate formula) provided to pre-term infants. Typically, the nutritional liquid is warmed in a neonate feeding syringe or warm nutritional liquid is poured into the syringe and then fed to the neonate. Unfortunately, even if the nutritional liquid is prewarmed to body temperature, the temperature of the nutritional liquid in the feeding syringe decreases to room temperature during feeding due to the long feeding time. The average feeding time is about 30 minutes to 4 hours. Heat is lost through the neonate feeding syringe. Also, heat is lost through a tube routed to the stomach of the neonate. In particular, as the nutritional liquid flows from the feeding syringe to the neonate through the tube, significant heat loss is experienced through the tubing since the nutritional liquid travels through the tubing at a relatively slow rate. Accordingly, even if the nutritional liquid in the neonate feeding syringe is raised to the body temperature of the mother, such warming is rendered ineffective since there is a significant temperature drop as the nutritional liquid flows through the tube.

Accordingly, there is a need in the art for an improved method and device for heating nutritional liquid fed to the pre-term infant.

BRIEF SUMMARY

The embodiments discussed herein address the needs discussed above, discussed below and those that are known in the art.

A heating system that includes a heater and a control module is disclosed herein. The control module controls operation of the heater. The heater is used to warm the nutritional liquid (e.g., breast milk or neonate formula) being fed to the neonate. In particular, the heater of the heating system is placed in close proximity to the neonate along a length of a tube being used to feed the neonate. Since the heater is in close proximity to the neonate on the tube, the temperature drop due to heat loss through the tube after the nutritional liquid is heated and travels to the neonate is minimal. Moreover, any heat loss from the syringe to the heater is inconsequential since the heater raises the temperature of the nutritional liquid to the desired target temperature immediately before the nutritional liquid reaches the neonate.

More particularly, a heating system for heating neonate nutritional liquid so that a temperature of the nutritional liquid is greater than room temperature when providing warmed nutritional liquid to the neonate during feeding is disclosed. The heater system may comprise a heater including a first heating portion having a first groove for receiving a tube; a first handle fixed to the first heating portion; a second portion disposable over the first groove; and a second handle fixed to the second portion.

The first heating portion and handle may be pivotally traverseable to the second portion and handle between open and closed positions. In the open position, the neonate feeding tube may be inserted or removed from the first groove. In the closed position, the second portion covers the first groove and the first heating portion warms the neonate nutritional liquid that flows through the tube.

The second portion may have a heating portion and a second groove for receiving the tube. The first and second grooves may collectively have a snug fit around the tube for transferring heat through the neonate feeding tube to the neonate nutritional liquid flowing through the neonate feeding tube. The first heating portion may comprise a first heater and a first heat conductor. The first groove may be formed in the first heat conductor. The second heating portion comprises a second heater and a second heat conductor. The second groove may be formed in the second heat conductor.

The first and second grooves may be straight and have matching semi-circular cross sectional configurations.

The first and second portions may be pivotally biased to the closed position. A spring may bias the first and second portions to the closed position.

The heating system may further comprise a control module including a rechargeable battery pack for providing electricity to the heater and a means for controlling the heater. The control module may include a readout for providing a temperature of the heater. The control module may also include a battery strength indicator. The control module and the heater may be in electrical communication with each other through a wire. The control module may be integrated into a body of the heater.

Additionally, a system for providing warm nutritional liquid to a neonate is disclosed. The system may comprise a neonate feeding syringe fillable with the nutritional liquid; a tube connected to the syringe and in fluid communication with a stomach of the neonate; a syringe pump wherein the syringe is mountable to the syringe pump which forces the nutritional liquid from the syringe through the tube to the neonate; a heater mounted about the tube and positioned closer to the neonate than the syringe pump along a length of the tube wherein the heater transfers heat through the tube and to the nutritional liquid flowing through the tube to minimize heat loss from the nutritional liquid after the nutritional liquid exits the heater and flows toward the neonate so that the nutritional liquid is provided to the neonate above room temperature.

The tube may be an extension tube and the heater may be positioned immediately adjacent to a distal end of the extension tube. The heater may abut the distal end of the extension tube.

The system may further comprise a feeding tube in fluid communication with the extension tube and the heater further. The heater may comprise a first heating portion having a first groove for receiving the extension tube; a first handle fixed to the first heating portion; a second portion disposable over the first groove; a second handle fixed to the second portion.

The first heating portion and handle may be pivotally traversable to the second portion and handle between open and closed positions. In the open position, the feeding tube or extension tube may be inserted or removed from the first groove. In the closed position, the second portion covers the first groove and the first heating portion warms the neonate nutritional liquid that flows through the extension tube or the neonate feeding tube.

Additionally, a system for providing warm nutritional liquid to a neonate is disclosed. The system may comprise a gravity feeding syringe fillable with the nutritional liquid; a tube connected to the syringe and in fluid communication with a stomach of the neonate; a stand for hanging the gravity feeding syringe above the neonate to flow the nutritional liquid from the syringe through the tube to the neonate; a heater mounted about the tube and positioned closer to the neonate than the syringe pump along a length of the tube. The heater transfers heat through the tube and to the nutritional liquid flowing through the tube to provide warm nutritional liquid to the neonate to minimize heat loss from the nutritional liquid after the nutritional liquid exits the heater and flows toward the neonate so that the nutritional liquid is provided to the neonate above room temperature.

The tube may be a feeding tube and the heater may be positioned immediately adjacent to the neonate so that a temperature of the nutritional liquid is above room temperature when the nutritional liquid reaches the neonate.

Additionally, a method of feeding a neonate with warm nutritional liquid is disclosed. The method may comprise the steps of filling a neonate feeding syringe with nutritional liquid; connecting a tube to the neonate feeding syringe; placing the tube in fluid communication with a stomach of the neonate; placing a heater on the tube for heating the nutritional fluid flowing through the tube, the heater being positioned on the tube closer to the neonate than the neonate feeding syringe along a length of the tube; flowing the nutritional liquid from the neonate feeding syringe, through the tube and to the neonate; and heating the nutritional liquid flowing through the tube with the heater so that a temperature of the nutritional liquid is above room temperature when the nutritional liquid reaches the neonate to facilitate digestion of the warm nutritional liquid by the neonate.

The flowing step may be accomplished with a syringe pump. The flowing step may also comprise elevating the neonate feeding syringe above the neonate to gravity feed the neonate.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
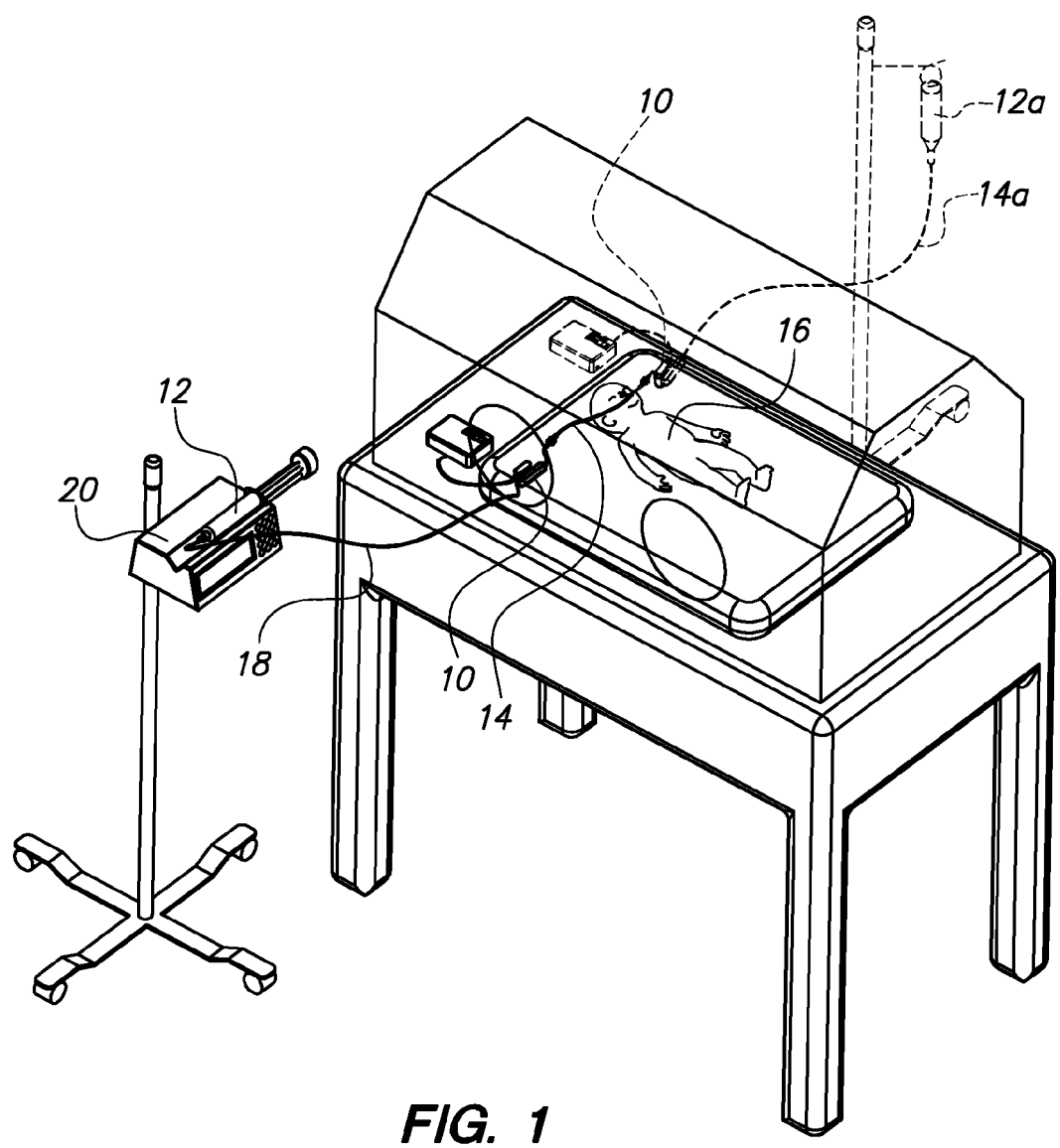
FIG. 1 illustrates a neonate being fed with a syringe pump or alternatively with a gravity syringe and a heating system disposed as close to the neonate so that the neonate is fed with nutritional liquid above room temperature and preferably at normal body temperature of a person.

Referring now to the drawings, an in-line neonatal fluid tubing heater 10, 10a is shown. A syringe 12, 12a is filled with a nutritional liquid (e.g., breast milk or neonate formula). From the syringe 12, 12a, the nutritional liquid flows through extension tube 18 and feeding tube 14 or feeding tube 14a. The heater 10 is mounted to the extension tube 18 or the feeding tube 14a to warm up the nutritional liquid flowing through the feeding tube 14, 14a above room temperature and preferably to about the body temperature of a person (i.e. between about 95° F. and about 99° F.). Feeding warm nutritional liquid to the neonate 16 facilitates digestion of the nutritional liquid and preserves the neonate's energy for healing and growth. The heater 10, 10a may be placed on the extension tube 18 or the tube 14a as close to the neonate 16 as possible to minimize a reduction in the temperature of the nutritional fluid as the nutritional liquid exits the heater 10, 10a on its way to the neonate 16. As the nutritional liquid flows through the heater 10, the heater 10 increases the temperature of the nutritional liquid to a temperature above room temperature and preferably to a temperature about the body temperature of the neonate 16.

As shown in FIG. 1, the neonate 16 may be fed nutritional liquid with a syringe 12 and syringe pump 20 or with a gravity syringe 12a. In relation to the syringe pump 20, the heater 10 is shown as being attached to the extension tube 18 instead of the feeding tube 14. However, it is also contemplated that the heater 10 may be mounted to the feeding tube 14 as close as possible to the neonate 16 in a similar fashion as the heater 10 described in relation to the gravity feeding method.

Figure 2:
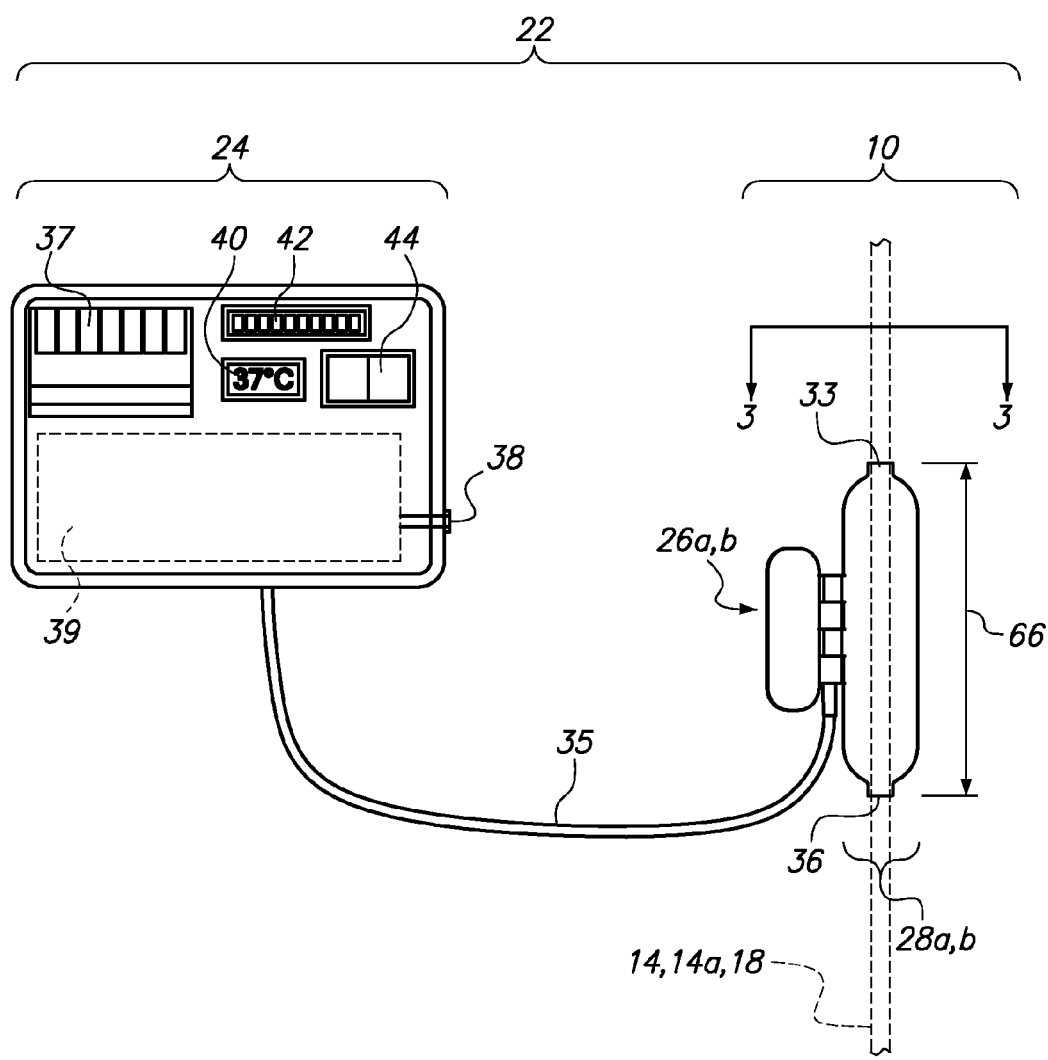
FIG. 2 illustrates the heating system having a heater and a control module.
Figure 3:
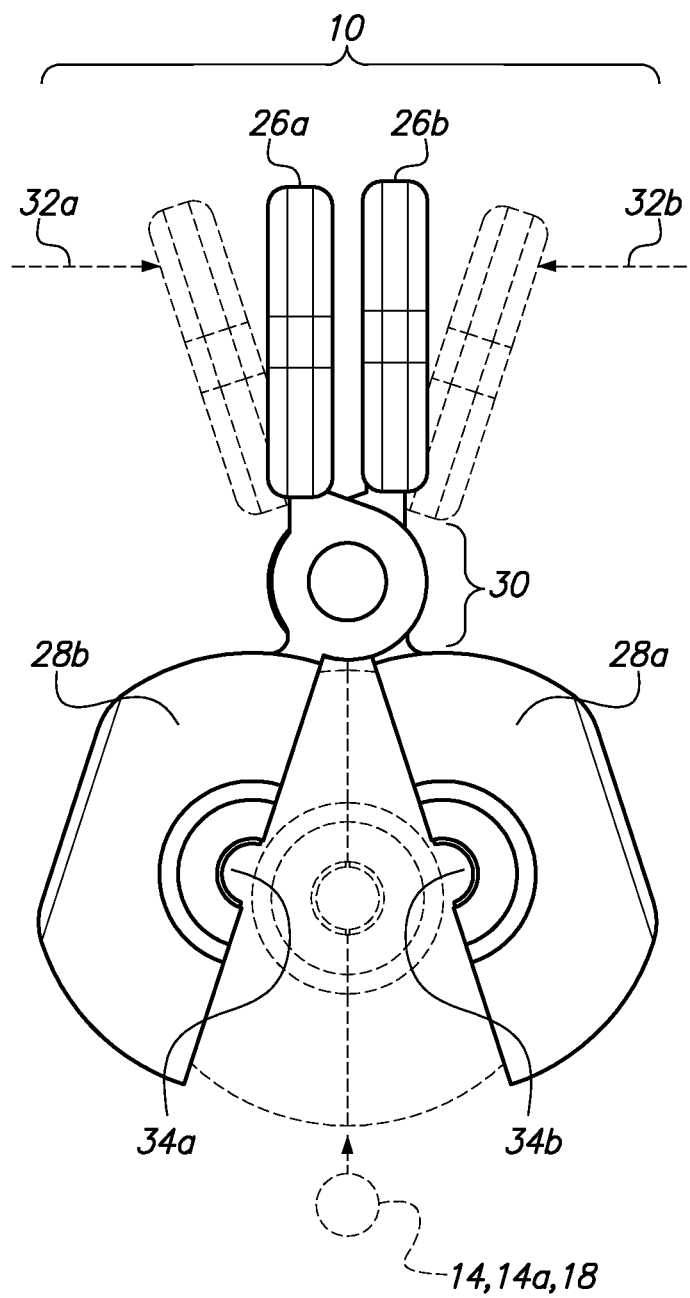
FIG. 3 is a side view of the heater shown in FIG. 2.

A heating system 22 is shown in FIG. 2. The heating system 22 may comprise the heater 10 and a control module 24. The heater 10 is shown in more detail in FIGS. 3 and 4. Referring to FIG. 3, the heater 10 may be traversed between the open and closed positions. The open position is shown in solid lines in FIG. 3. The closed position is shown in dash lines in FIG. 3. The first and second handles 26a, b and first and second heating portions 28a, b may be biased to the closed position as shown in dash lines in FIG. 3. The handles 26a, b and heating portions 28a, b may be biased to the closed position by way of a torsion spring 63 (see FIG. 4) fitted within hinge 30. From the closed position shown by the dash lines, a person may grip the first and second handles 26a, b and apply opposing compressive forces 32a, b to overcome the biasing force and open the first and second heating portions 28a, b. The feeding tube 14, 14a or extension tube 18 may be fitted within the heating portions 28a, b to heat nutritional liquid that flows through the tubes 14, 14a, 18. When the tubes 14, 14a, 18 are fitted within the first and second heating portions 28a, b, the user may release the first and second handles 26a, b to clamp the first and second heating portions 28a, b about the tube 14, 14a, 18. Each of the heating portions 28a, b may have a straight elongated groove 34a, b that extends along the length 66 of the heating portions 28a, b as shown in FIGS. 2 and 3. The heating portions 28a, b may be sufficiently long so that heat can be transferred into the nutritional liquid as the nutritional liquid flows through the tube 14, 14a, 18 between an entrance 33 and exit 36 (see FIG. 2) of the heating portions 28a, b. The heater 10 may also be in electrical communication with the control module 24 through cable 35. The control module 24 is capable of controlling the heating portions 28a, b by way of heater controller 37. The heater 10 and the control module 24 may be powered by rechargeable batteries 39. The rechargeable batteries 39 may be recharged by way of a charger connected to a battery recharge port 38. A readout 40 (e.g., digital readout) provides the temperature of the heating portions 28a, b. Battery strength/charging indicator 42 may also be provided on the control module 24. The control module 24 and the heater 10 may be turned on and off by way of an on/off switch 44.

During use, the operator squeezes the handles 26a, b together to traverse the heater 10 to the open position as shown in FIG. 3. With the heater 10 in the open position, the operator inserts the tube 14, 14a, 18 into the first and second grooves 34a, b. In particular, the tube 14, 14a, 18 is inserted into one of the grooves 34a, 34b. Once the tube 14, 14a, 18 is placed in the groove 34a or 34b, the operator releases the first and second handles 26a, b to traverse the heater portions 28a, b to the closed position. In the closed position, the tube 14, 14a, 18 is nested within the grooves 34a, b. Preferably, the heater portions 28a, b contact and press against tube 14, 14a and 18 to provide as much heat to the nutritional liquid flowing through the tube 14, 14a, 18.

Referring now to FIG. 2, once the tube 14, 14a, 18 is placed in the heater 10, the operator turns on the control module 24 by toggling switch 44 to the on position. The user adjusts the temperature at which the heater 10 will heat the nutritional liquid by manipulating buttons of the heater controller 37. The operator either increases or decreases the maximum temperature of the heater 10. The maximum temperature is shown on the readout 40. The heater 10 and the control module 24 have a feedback loop which allows the control module 24 to control the maximum temperature of the heater 10. Additional toggle buttons and/or readouts 40 may be mounted to the control module 24 so that the readouts 40 can also provide the current temperature of the heater 10. Additional temperature sensors may be mounted to the heater 10, 10a to sense a temperature of the nutritional fluid flowing through the tube 14, 14a, 18. The control module 24 and the heater 10 are portable in that the control module 24 and the heater 10 may be powered by a battery pack 39. The remaining power in the battery pack 39 may be indicated by indicator 42. Also, the battery pack 39 may be recharged by connecting the battery pack 39 to a battery charger by way of recharge port 38.

Figure 4:
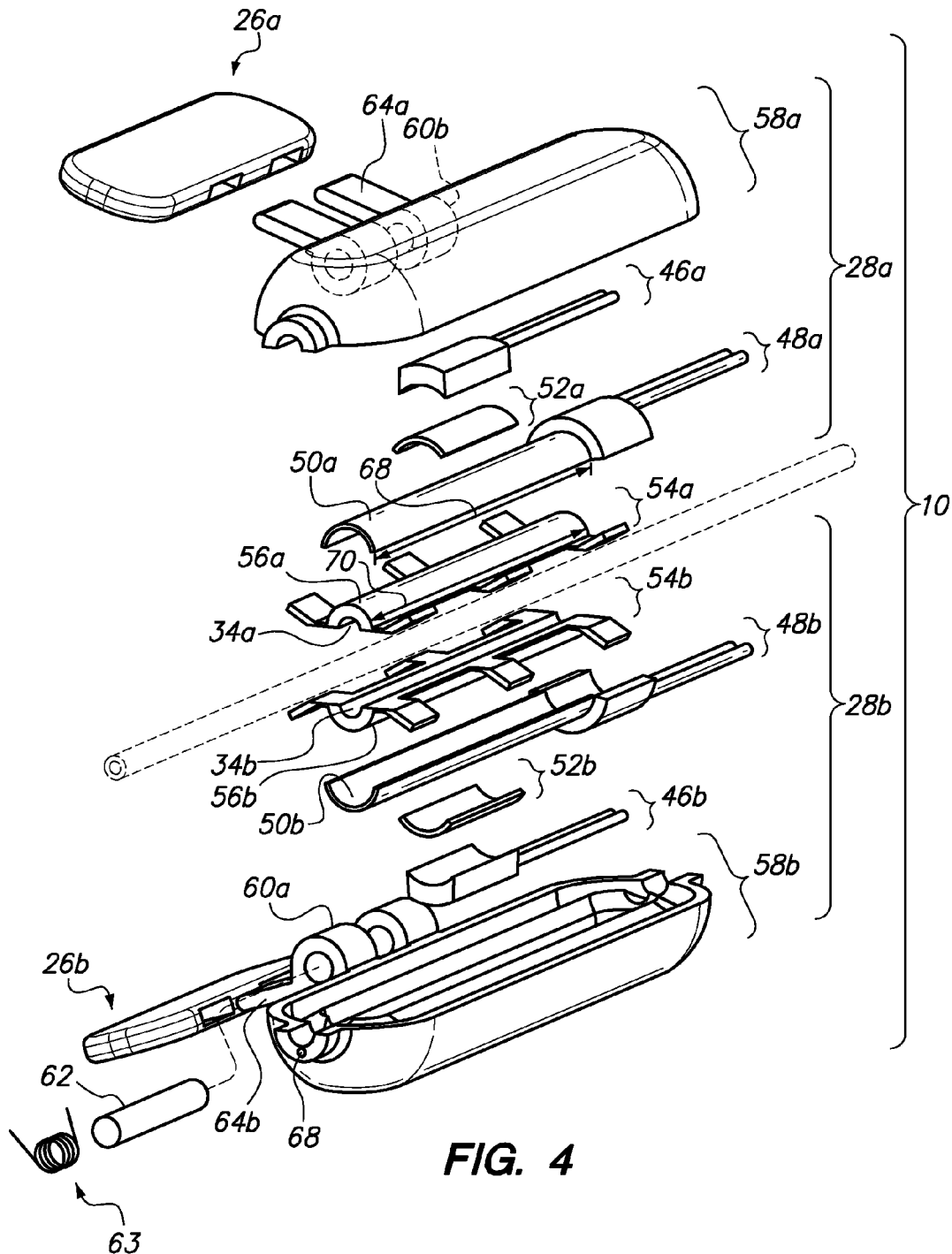
FIG. 4 is an exploded perspective view of the heater shown in FIGS. 1-3.

Referring now to FIG. 4, an exploded view of the heater 10 is shown. The first and second heating portions 28a, b may have first and second thermistor thermocouples 46a, b. The first and second heating portions 28a, b may additionally have first and second heaters 48a, b. The first and second thermocouples 46a, b and heaters 48a, b may be in electrical communication with the control module 24. When the operator turns on the control module 24, the control module 24 may send power to the heaters 48a, b to increase the temperature of the heating portions 50a, b. The thermocouples 46a, b take the reading of the temperature of the heating portions 50a, b and send that information to the control module 24. The temperature of the heating portions 50a, b may be displayed on the readout 40. If the thermocouple 46a, b indicates that the heating portions 50a, b have reached the maximum temperature set by the operator, then the control module 24 modulates the power supplied to the heaters 48a, b so that the temperature of the heating portions 50a, b is maintained at about the maximum temperature set by the operator.

Optionally, a temperature sensor 68 may be located adjacent the exit 36 of the heater 10, 10a. The sensor 68 may sense a temperature of the nutritional fluid flowing through the tube 14, 14a, 18 as the nutritional fluid flows out of the heater 10, 10a. The temperature sensor 68 may send a signal to the control module 24 which may be programmed to modulate power to the heater 10, 10a based on the sensed temperature of the nutritional liquid instead of the sensed temperature of the heating element 50a, b.

First and second insulators 52a, b may be disposed between the thermocouples 46a, b and the heating portions 50a, b. The heating portions 50a, b may be a Kapton (i.e., polyimide) heater. The heating portions 50a, b may have a curved semi-cylindrical configuration as shown in FIG. 4. Heat sinks 54a, b may be disposed on the inside of the heating portions 50a, b. The heat sinks 54a, b may define the straight grooves 34a, b of the first and second heating portions 28a, b. The straight grooves 34a, b may have a semi-circular cross sectional configuration so as to receive the tube 14, 14a and 18 which preferably has a cylindrical cross section. The back side 56a, b may have a curved configuration and receive the heating portions 50a, b. The heating portions 50a, b may be mounted to the back sides 56a, b of the heating portions 50a, b through methods known in the art or developed in the future.

The heaters 48a, b, the heat sinks 54a, b, the insulation 52a, b and the thermocouples 46a, b may all be mounted within respective outer cases 58a, b. The outer cases 58a, b may have first and second hinge elements 60a, b. The hinge elements 60a, b may be nested together and held together by pin 62. A torsion spring 63 may be mounted to the hinge elements 60a, b to bias the heating portions 28a, b to the closed position. The outer cases 58a, b may additionally have support members 64a, b that are received into the first and second handles 26a, b for mounting the outer cases 50a, b to the handles 26a, b.

Figure 5:
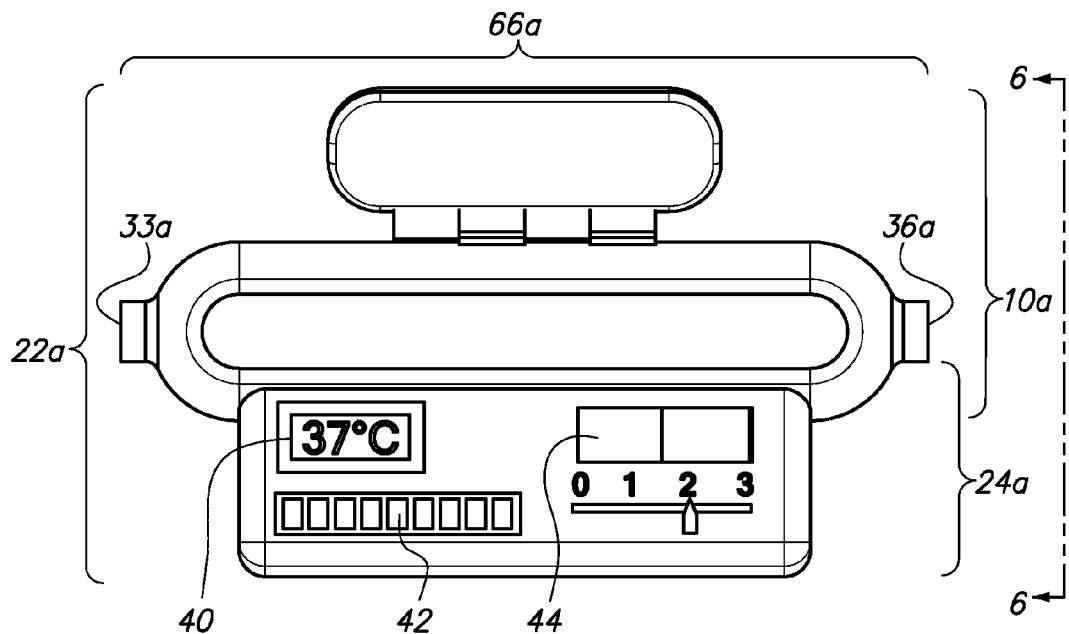
FIG. 5 is an illustration of a second embodiment of the heating system with the control module integrated into the heater.
Figure 6:
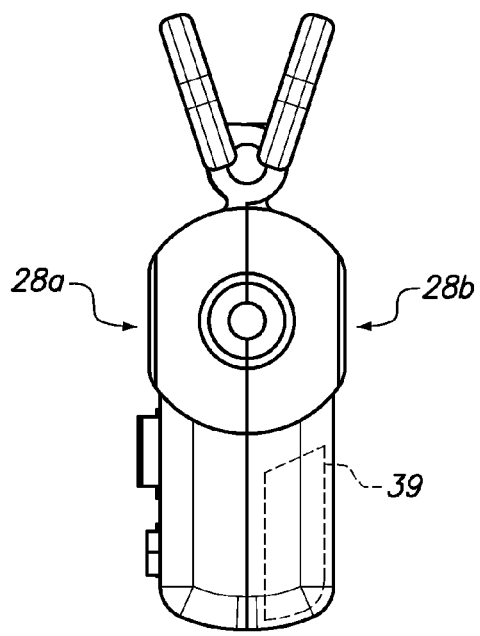
FIG. 6 is a side view of the second embodiment of the heating system shown in FIG. 5.

Referring now to FIGS. 5 and 6, a second embodiment of the heating system 22a is shown. The heating system 22a has a heater 10a and a control module 24a which are integrated to each other. As shown in FIG. 6, the control module 24a may be integrated into one or both of the heating portions 28a, b. The control module 24a may have the readout 40, indicator 42 and on/off switch 44 integrated into the first heating portion 28a. Battery pack 39 may be integrated into the second heating portion 28b. The electronics for the readout 40, indicator 42 and the on/off switch 44 may be in electrical communication with the battery pack 39. Moreover, the battery pack 39 may be in electrical communication with the heater 48a, b and the thermocouple 46a, b mounted within the outer cases 58a, b of the first and second heating portions 28a, b. The heating system 22a may operate in substantially the same manner as that described in relation to heating system 22 except that the control module 24 is integrated into the heater 10a.

The heater 10, 10a discussed herein may be placed as close to the neonate 16 as possible. This does not mean that the heater 10, 10a is placed on the tube 14, 14, 18 away from the neonate and the tube 14, 14a, 18 is bent so that the heater 10, 10a is located closely adjacent to the heater 10, 10a. Instead, this means that the distance that the nutritional liquid fluid flows from the heater 10, 10a to the neonate 16 through the tube 14, 14a, 18 is minimized by placing the heater 10, 10a as close to the neonate along a length of the tube 14, 14a, 18. The extension tube 18, feeding tube 14, 14a have a linear length. The heater 10, 10a may be placed on the tube 14, 14a, 18 at any position along the length of the tube 14, 14a, 18. However, as discussed herein it is advantageous that the heater 10, 10a be placed near the neonate 16 along the length of the tube 14, 14a, 18. By placing the heater 10, 10a closer to the neonate 16 the distance that the nutritional liquid travels to reach the neonate 16 after the nutritional liquid exits the heater 10, 10a is minimized so that heat loss through the tube is neglible. For example, after the nutritional liquid exits the heater 10, 10a the heat in the nutritional liquid begins to be transferred to the environment thereby cooling the nutritional liquid. By the time the nutritional liquid reaches the neonate 16, the nutritional liquid has a lower temperature than when the nutritional liquid exited the heater 10, 10a. Nonetheless, the nutritional liquid is above room temperature and is preferably about equal to the body temperature of. If the temperature drop from the heater 10, 10a to the neonate 16 is significant, it is contemplated that the heater 10, 10a may raise the temperature of the nutritional liquid to a temperature above the body temperature of a human. In this manner, as the nutritional liquid flows from the heater 10, 10a towards the neonate 16, the temperature of the nutritional liquid cools down to about the body temperature of a person.

The heater 10, 10a may be sufficiently long so that the nutritional liquid can be heated to the target temperature of the neonate. The heater 10, 10a has a particular length 66, 66a as shown in FIGS. 2 and 5. The nutritional liquid flows into the heater 10, 10a from the entrance 33,33a and leaves out of exit 36, 36a. However, the actual heating portions have a length 68 (see FIG. 4) which is shorter than the length 66 of the heater 10, 10a. The heater 10, 10a is mounted to a heat conductor 54a, b. The heat conductors 54a, b heat up the nutritional liquid flowing through the tube 14, 14a, 18. A length 70 of the heat conductor 54a, b defines a heating region which heats up the nutritional liquid flowing through the tube 14, 14a, 18. The heating region may be sufficiently long to gradually raise the temperature of the nutritional liquid. If the length 70 of the heating region is too short, then the temperature of the nutritional liquid must be raised at a rapid rate which may require the heating portions 50a, b to be set at a high temperature. In this case, the nutritional liquid may be exposed to excessively high temperatures that may destroy immunological properties of the nutritional liquid. Accordingly, the length 70 of the heating region is sufficiently long so that the maximum temperature of the heating portions 50a, b may be reduced to a temperature which is safe for the nutritional liquid and can still raise the temperature of the nutritional liquid to the target temperature (e.g., body temperature, temperature above body temperature) at a reasonable rate.

As discussed herein the grooves 34a, b of the heating portions 28a, b that receive the tube 14, 14a, 18 may be straight. However, other shapes are also contemplated. By way of example, other shapes include but is not limited to Z shaped, L shaped, U shaped.

The above description is given by way of example, and not limitation. Given the above disclosure, one skilled in the art could devise variations that are within the scope and spirit of the invention disclosed herein, including various ways of flow nutritional fluid through the tube 14, 14a, 18. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of feeding a neonate with warm nutritional liquid, the method comprising the steps of:
    filling a neonate feeding syringe with nutritional liquid;
    connecting a tube to the neonate feeding syringe;
    placing the tube in fluid communication with a stomach of the neonate;
    placing a heater on the tube for heating the nutritional fluid flowing through the tube, the heater being positioned on the tube closer to the neonate than the neonate feeding syringe along a length of the tube for feeding the neonate with warm nutritional liquid before the nutritional cools down as the nutritional fluid travels through the tube from the heater to the stomach of the neonate;
    flowing the nutritional liquid from the neonate feeding syringe, through the tube and to the neonate;
    heating the nutritional liquid flowing through the tube with the heater so that a temperature of the nutritional liquid is above room temperature when the nutritional liquid reaches the neonate to facilitate digestion of the warm nutritional liquid by the neonate.

2. The method of claim 1 wherein the tube is a feeding tube and the heater is positioned immediately adjacent to the neonate.

3. The method of claim 1 wherein the flowing step is accomplished with a syringe pump.

4. The method of claim 1 wherein the flowing step comprising elevating the neonate feeding syringe above the neonate to gravity feed the neonate.

* * * * *